United States Patent
Cairns (10) Patent No.: US 10,456,571 B2
(45) Date of Patent: Oct. 29, 2019

(54) SEALABLE, PENETRABLE INTERFACE AND METHODS OF MAKING AND USING SAME

(71) Applicant: STILLWATER TRUST, Ormond Beach, FL (US)

(72) Inventor: James L. Cairns, Ormond Beach, FL (US)

(73) Assignee: Stillwater Trust, Ormond Beach, FL (US)

( * ) Notice: Subject to any disclaimer, the term of this patent is extended or adjusted under 35 U.S.C. 154(b) by 0 days.

(21) Appl. No.: 15/861,098

(22) Filed: Jan. 3, 2018

(65) Prior Publication Data

US 2018/0193627 A1 Jul. 12, 2018

Related U.S. Application Data

(60) Provisional application No. 62/443,968, filed on Jan. 9, 2017.

(51) Int. Cl.
*A61M 39/06* (2006.01)

(52) U.S. Cl.
CPC ... *A61M 39/0606* (2013.01); *A61M 2039/062* (2013.01); *A61M 2039/0626* (2013.01); *A61M 2039/0653* (2013.01)

(58) Field of Classification Search
CPC . A61B 1/018; A61B 1/00137; A61B 17/3462; A61B 17/3498; A61B 1/2676; A61B 1/00128; A61B 1/012; A61B 2017/3437; A61B 17/3421; A61B 90/50; A61B 17/3417; A61B 1/0014; A61B 1/00147; A61B 1/0052; A61B 90/57; A61B 10/0233; A61B 10/0275; A61B 10/0283; A61B 17/3474; A61B 1/00133; A61B 5/06; A61B 90/53; A61B 10/04; A61B 17/221; A61B 1/00091; A61B 1/00096; A61B 1/0125; A61B 1/015; A61B 1/0661; A61B 1/126; A61B 1/2733; A61B 1/2736; A61B 1/31; A61B 2017/347; A61B 2090/3614; A61B 5/065; A61B 17/3403; A61B 17/3423; A61B 17/3431; A61B 17/3468; A61B 17/3494; A61B 17/3496;

(Continued)

(56) References Cited

U.S. PATENT DOCUMENTS

| 787,348 A | 4/1905 | Hansen |
| 3,986,508 A | 10/1976 | Barrington |

(Continued)

OTHER PUBLICATIONS

Notice from the Search Authority for International Patent Application No. PCT/US2018/012184 dated Mar. 6, 2018.

(Continued)

*Primary Examiner* — Brandy S Lee
(74) *Attorney, Agent, or Firm* — Mark T. Vogelbacker (57) ABSTRACT

A penetrable interface configured to separate two or more spaces can include an elastomeric seal having a first segment and a second segment. A portion of the second segment can be integrally formed with a portion of the first segment. The first and second segments can create a sealing engagement therebetween in the absence of an applied force on the second segment. The first and second segments can be distorted out of sealing engagement when subjected to the applied force on the second segment.

10 Claims, 5 Drawing Sheets

(58) Field of Classification Search
CPC ... A61B 1/0005; A61B 1/00154; A61B 1/042; A61B 1/05; A61B 1/273; A61B 2017/00243; A61B 2017/00296; A61B 2017/00477; A61B 2017/00703; A61B 2017/0243; A61B 2017/22071; A61B 2017/3405; A61B 2017/3407; A61B 2017/3409; A61B 2017/3484; A61B 2017/3492; A61B 2034/105; A61B 2034/2059; A61B 2090/034; A61B 2090/062; A61B 2090/365; A61B 2090/373; A61B 34/30; A61B 34/76; A61B 50/20; A61B 5/0059; A61B 5/055; A61B 5/062; A61B 5/150748; A61B 5/415; A61B 5/418; A61B 5/489; A61B 6/032; A61B 6/037; A61B 8/13; A61B 90/13; A61M 2025/09125; A61M 25/02; A61M 25/0618; A61M 25/09041; A61M 39/04; A61M 39/0606; A61M 2025/0183; A61M 25/0097; A61M 25/0169; A61M 25/0172; A61M 5/3273; A61M 25/0606; A61M 2039/062; A61M 2039/0633; A61M 2039/064; A61M 39/1011; A61M 2039/0653; A61M 2039/0686; A61M 2205/273; A61M 39/06; A61M 39/20; A61M 5/321; A61M 2025/0057; A61M 2025/0089; A61M 2025/1013; A61M 2025/105; A61M 2025/1075; A61M 2025/1081; A61M 2039/0072; A61M 2039/1016; A61M 2039/1033; A61M 25/00; A61M 25/0021; A61M 25/0045; A61M 25/0105; A61M 25/0133; A61M 25/04; A61M 25/0625; A61M 25/0668; A61M 25/10; A61M 25/1011; A61M 37/0069; A61M 39/0693; A61M 39/10; A61M 5/3287; A61M 5/427; A61M 2039/0626

See application file for complete search history.

(56) References Cited

U.S. PATENT DOCUMENTS

| | | | | |
|---|---|---|---|---|
| 4,080,965 | A | 3/1978 | Phillips | |
| 4,387,879 | A | 6/1983 | Tauschinski | |
| 5,743,884 | A | 4/1998 | Hasson et al. | |
| 6,033,426 | A | 3/2000 | Kaji | |
| 7,722,575 | B2 | 5/2010 | Lopez | |
| 8,753,317 | B2 * | 6/2014 | Osborne | A61M 39/0606 604/164.01 |
| 2002/0156430 | A1 * | 10/2002 | Haarala | A61M 25/0075 604/247 |
| 2004/0126742 | A1 * | 7/2004 | Heasley | A61C 3/00 433/159 |
| 2005/0171489 | A1 * | 8/2005 | Weaver | A61M 39/24 604/247 |
| 2010/0063364 | A1 | 3/2010 | Bonadio et al. | |
| 2011/0022068 | A1 | 1/2011 | Alghamdi | |
| 2011/0313368 | A1 * | 12/2011 | Weaver | A61M 25/0097 604/247 |

OTHER PUBLICATIONS

International Search Report and Written Opinion for International Patent Application No. PCT/US2018/012184 dated May 1, 2018.

\* cited by examiner

SEALABLE, PENETRABLE INTERFACE AND METHODS OF MAKING AND USING SAME

CROSS-REFERENCE TO RELATED APPLICATION

This application claims priority to U.S. Provisional Patent Application No. 62/443,968 filed on Jan. 9, 2017, the disclosure of which is incorporated by reference herein.

FIELD OF THE PRESENTLY DISCLOSED TECHNOLOGY

Embodiments of the presently disclosed technology relate to an apparatus, system, and method for passing one or more objects, such as elongated objects in the form of medical instruments or injection/withdrawal tubes, through an interface while the interface remains sealed from the ambient environment and preventing the passage of other objects or fluids before, during, and after use.

The presently disclosed technology is a fundamental building block that will find use in a wide variety of fields and applications. Some of its potential applications are herein described for the field of medicine, although it will be clear that its uses go far beyond that field.

BACKGROUND

There are many practical applications requiring the insertion and/or withdrawal of elongated objects through an interface while maintaining the interface sealed. For example, medical devices, such as optical or electrical probes or miniature surgical tools, must often be inserted or removed through a tubular conduit sealably connected to a patient. In other instances, fluids themselves must be repeatedly injected or withdrawn from a patient, requiring a sealed connection, such as between a catheter and a bodily-fluid collection container, or at the junction between an injection device and the conduit where fluids are introduced into the patient. Such interventions often require a sealed interface that can remain in place, yet can be penetrated over and over by a tubular or solid object. Other desirable attributes of such penetrable interfaces are that they block the siphoning of contaminants into the patient once the object is withdrawn from the sealed interface, and they do not permit outflow of bodily fluids from the patient once the object is withdrawn. Still other attributes of such sealed interfaces are that, for purposes of repeated patient intervention, they must be reliable, reusable, and easily disinfected between uses.

Presently available technology offers a variety of means to accomplish medical interventions such as those just described; however, there are some ubiquitous disadvantages to the existing art. Foremost among them is their relative complexity, which makes them expensive, difficult to manufacture, and hard to clean. Some employ one or more stacked, linearly slitted elastomeric seals in various configurations such as described in U.S. Pat. Nos. 4,387,879, 5,743,884, 6,033,426, and US 2010/0063364. Seals with linear slits are problematic at least because they do not always snap closed immediately due to weak restoring forces supplied only by the tendency of the slits to return elastically to the closed position, and they do not seal well to cylindrical objects inserted through them. Linear slits result in eye-shaped openings whose extremes do not conform to inserted cylindrical objects. So linear slits do not seal tightly, and if there is a pressure differential across linear slits, it results in leakage past the interface. Stacking slitted seals does not completely solve the leakage associated with the nonconformity.

Other penetrable interfaces use one or more elastomeric barriers puncturable by sharp spikes, such as illustrated in U.S. Pat. Nos. 3,986,508, 4,080,965, and 7,722,575. Elastomeric barriers that are perforated by sharp spikes, hypodermic needles for instance, are degraded with each use. So their reliable reuse is not guaranteed.

Neither of the abovementioned sealed interface structures is ideal due to the reasons stated. Many medical devices of this general sort are used once and then discarded, so expense is an important factor favoring simple, economical products.

SUMMARY

Noting the shortcomings of existing art, it's clear that a sealed, uncomplicated, penetrable interface that is reliable, easily and rapidly penetrated, easily cleanable, reusable through many uses, does not siphon, and/or remains sealed up to a chosen differential pressure, would be very useful in many medical procedures.

The sealed interface of the presently disclosed technology can include an elastomeric barrier that permits sealable insertion of an object such as an elongated tube through it, and returns to a sealed, closed condition when the object is withdrawn. The barrier can include a movable segment in the form of a crescent shaped perforation cut completely therethrough. No material needs to be removed from the barrier when the crescentic cut is made. The perforation can define a plug-like element, hereinafter called the tap, and a bore. Both the tap and bore can remain integral portions of the barrier, hereinafter referred to also as the seal. The tap can remain sealably closed and in the bore when no object is inserted through the bore, and can distort to unseat from the bore when the bore is penetrated by an elongated object. During withdrawal of the object, the tap can return immediately to its seat and, in the process, be at least slightly compressed as it is moved back into the bore such that the tap can "squeegee" the bore clean. This one-piece construction eliminates many of the complexities of existing penetrable interfaces while satisfying the desired attributes of reliability, ease and rapidity of penetration and cleaning, reusability, non-siphoning, and sealing up to a preset differential pressure both during penetration, when penetrated, and after the penetrating object is withdrawn.

In one embodiment, the presently disclosed technology is directed to a penetrable interface configured to separate two or more spaces. The interface can include an elastomeric seal having a first segment and a second segment. A portion of the second segment can be integrally formed with a portion of the first segment. The first and second segments can create a sealing engagement therebetween in the absence of an applied force on the second segment. The first and second segments can be distorted out of sealing engagement when subjected to the applied force on the second segment.

In another embodiment, the presently disclosed technology is directed to an apparatus configured to sealably connect two or more spaces. The apparatus can include a housing defining a passageway and a retainer having an opening extending therethrough. The retainer can be removably attachable to the housing. The apparatus can also include an elastomeric seal configured to be positioned between the housing and the retainer. The seal can include a first segment and a second segment. A portion of the second segment can be integrally formed with a portion of the first segment. The first and second segments can create a sealing engagement therebetween in the absence of an applied force on the second segment. The first and second segments can be distorted out of sealing engagement subjected to the applied force on the second segment.

The presently disclosed technology can also be directed to a method of making a penetrable interface configured to separate two or more spaces. The method can include placing an elastomeric seal against a base, and forcing a punch through at least a portion of the elastomeric seal. The punch can include a sharpened edge having a gap therein. The gap can be one of a cut-out and a dull edge.

BRIEF DESCRIPTION OF THE DRAWINGS

The presently disclosed technology is presented herein in general terms without regard to any specific application. It will be easily understood that the described apparatus can be readily adapted to a wide variety of housings, retainers, bore arrangements, sizes, materials, and/or exterior configurations, making it adaptable to a broad spectrum of applications such as those wherein sealed connectors are advantageous. Furthermore, the presently disclosed technology can be useful in sealably enclosing electrical junctions, such as electrical connections of underwater connectors, instruments or other devices. The presently disclosed technology's salient features and advantages will become readily apparent to those of ordinary skill in the art after reviewing the following detailed description in light of the accompanying drawings, in which like reference numbers refer to like parts, and in which.

DETAILED DESCRIPTION

Certain terminology is used in the following description for convenience only and is not limiting. The words "forward" and "rearward" (and derivations thereof) designate directions in the drawings to which reference is made. Unless specifically set forth herein, the terms "a," "an" and "the" are not limited to one element but instead should be read as meaning "at least one." The terminology includes the words noted above, derivatives thereof and words of similar import.

Figure 1:
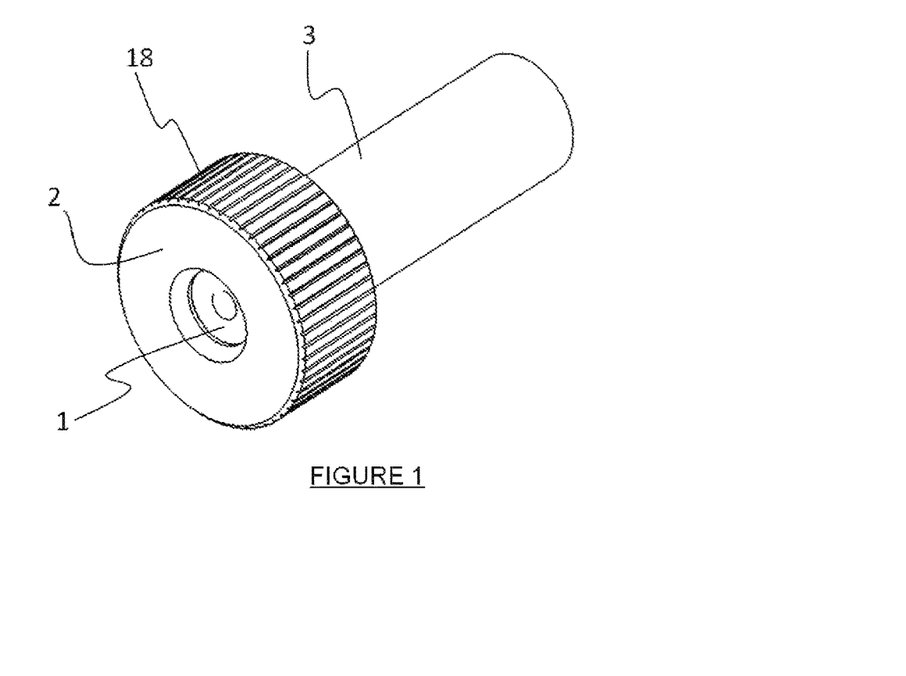
FIG. 1 is a perspective view of a sealed penetrable interface according to one embodiment of the presently disclosed technology as it might be incorporated into a larger assembly.
Figure 2:
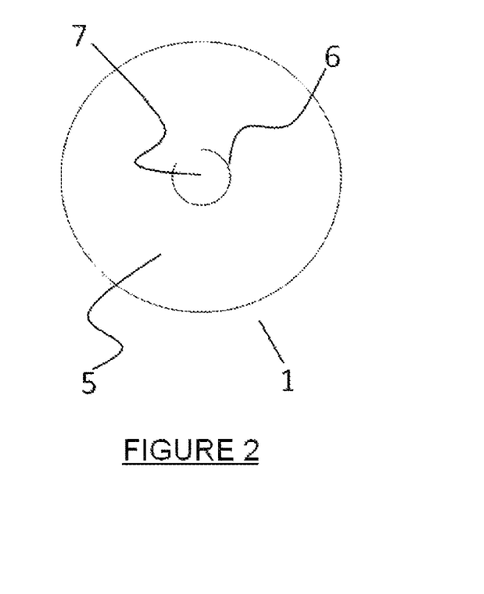
FIG. 2 is a face view of an elastomeric barrier of the assembly of FIG. 1.

The operation of the presently disclosed technology when used to permit insertion of elongated objects, for example, therethrough will now be described in detail. A generic rendition of the penetrable interface as it might be mounted into an assembly is illustrated in FIG. 1, wherein item 1 is an elastomeric seal, item 2 is a retainer nut, and item 3 is a portion of a housing into which the seal is mounted. Seal 1 is shown in greater detail in the various views depicted in FIGS. 2 and 3, but seal 1 is not limited to the circular or cylindrical shape shown. Seal 1 is also not limited to use only with nut 2 and housing 3, as seal 1 can be used with many other combinations of items. Seal 1 is shown herein as a circular object, but seal 1 can take the form of virtually any shape. The front elevational view of seal 1 shows on a first segment, face 5, the outline of perforation 6, which can form a crescent-shape. However, perforation 6 can form other shapes. Perforation 6 cuts axially through the entire thickness of seal 1, not necessarily with a circular or uniform diameter, thereby resulting in second segment or tap 7, and bore 8. Thus, face 5 and tap 7 are integrally or monolithically formed, but are configured to be moved with respect to each other without compromising the connection therebetween.

Figure 3:
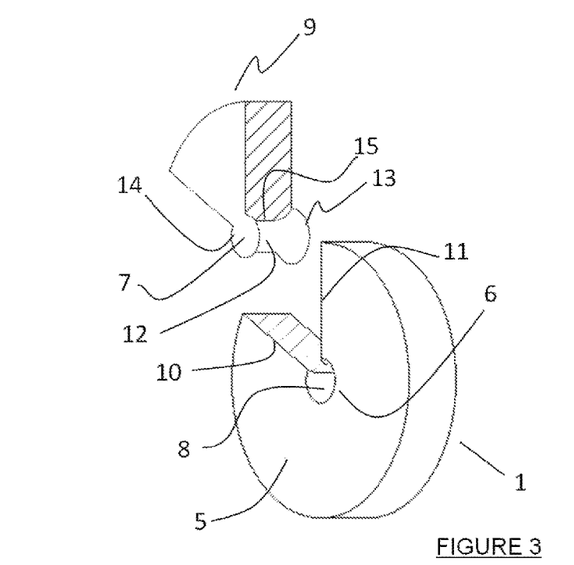
FIG. 3 is an oblique view of the barrier in FIG. 2, shown for purposes of illustration, only, with a section removed.

Seal 1 and its integral parts are easier to visualize by the oblique view of FIG. 3 in which, for purposes of better understanding, a portion 9 is shown cut away axially from seal 1 along lines 10, 11 which radiate outwardly from the ends of crescentic perforation 6. In FIG. 3, cutaway portion 9 is shown displaced radially outward from the remainder of seal 1 for clarity and purpose of illustration only. Tap 7 can include central portion 12 having first flared segment 13 on one end, and another or second flared segment 14 on the other or opposite end of central portion 12. In one embodiment, flared segments 13, 14 of second segment or tap 7 mirror flared ends of bore 8, from which the tap is cut or formed. In one embodiment, tap 7 remains attached to the main portion of seal 1 by uncut portion 15 of perforation 6. Uncut portion 15 provides a substantial elastic force to return tap 7 to its at-rest or initial position within bore 8 in the absence of externally applied forces.

Figure 10:
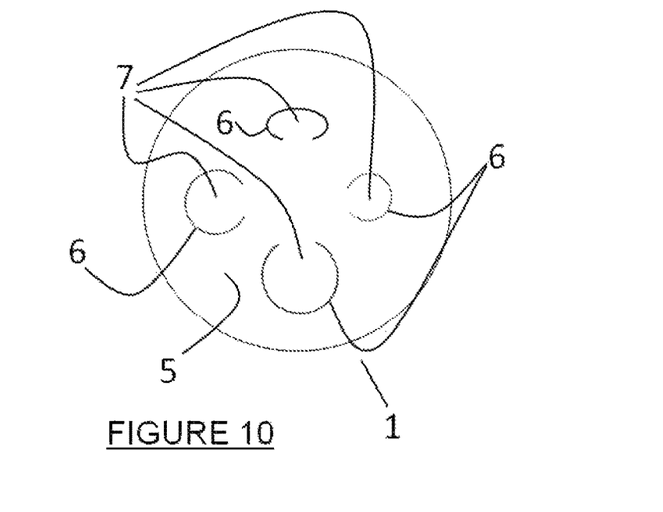
FIG. 10 is a face view of an elastomeric barrier having multiple penetration points each consisting of a tap and bore.

A sealed penetrable interface is not limited to one penetration point. FIG. 10 shows a seal similar to that of FIG. 2, having multiple (e.g., two or more), spaced-apart penetrable points through face 5, each consisting of a bore 8 (not shown) and a tap 7 defined by crescentric perforation 6, wherein each bore and tap can be sized and shaped to accommodate a respective probe. The multiple penetrable points can be evenly spread-out or inconsistently spread-out on the face.

Figure 4:
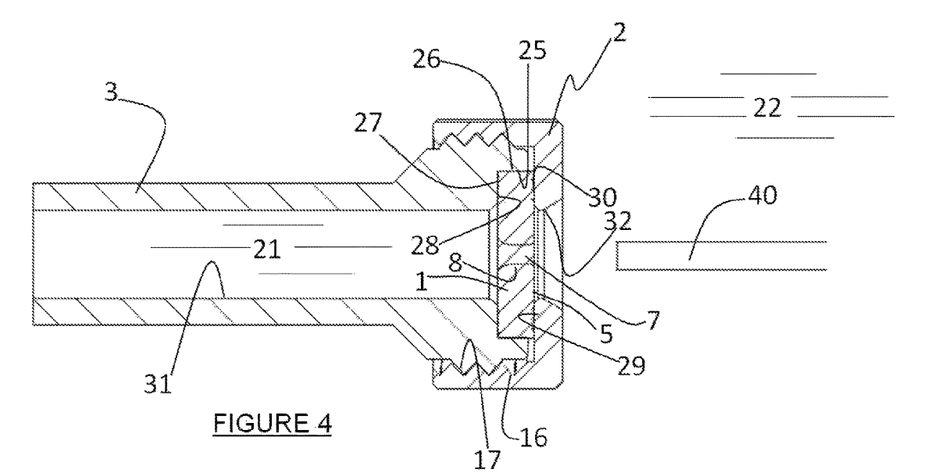
FIG. 4 is an axial half-section of the assembly of FIG. 1 when the interface is not penetrated.

FIG. 4 is an axial half-section view of a generic rendition of the presently disclosed technology illustrating the positions and interactions of the three elements it can include: seal 1, retainer nut 2, and housing 3. In one embodiment, nut 2 engages housing 3 by way of cooperating threads 16 on nut 2, and 17 on housing 3. However, nut 2 and housing 3 can engage in any of a variety of ways. One or more ridges 18 may be formed on an exterior of nut 2 to assist a user or a tool in grasping and/or holding nut 2. Exposed face 5 of seal 1 can be sealed, flat, and/or smooth when seal 1 is not penetrated, and therefore face 5 can be easily swabbed for disinfection. As a result, in such an embodiment no cap is required when the device is not in use, as the device can remain sealed and easily cleaned without a cap. A first space 21 internal to housing 3 is configured to be isolated from a second space 22 exterior to housing 3.

In one embodiment, seal 1 is confined or held in position by inner surface 25 of recess or socket 26 and wall 27 of housing 3 with forwardly raised circular nibs 28, and by wall 29 internal to nut 2 with raised circular nibs 30. Nibs 28 and 30 serve to grip the forward and rearward surfaces of seal 1 in order to maintain it in position while substantially or completely preventing leakage past the seal. Diameter 31 of passageway 21 of housing 3 and diameter 32 of the opening of nut 2 can be sized so as not to interfere with the actuation or movement of tap 7. It is understood by those skilled in the art that in an alternative embodiment the recess for seal 1 can be formed in nut 2 instead of housing 3.

In FIG. 4 seal 1 is shown not activated or opened; tap 7 is seated within bore 8, thereby preventing the flow of fluid through the bore 8 in the absence of an applied force on seal 1. In one embodiment, flared end segments 13, 14, (FIG. 3) of tap 7 aid in centering the tap axially within bore 8, and enhance both the wiping and sealing functions of the tap. A solid object, such as probe 40, is shown positioned in second space 22 ready to penetrate the sealed barrier via bore 8. Probe 40 is not limited to having a circular or round cross-section, but can be of any cross-sectional shape such that seal bore 8 can elastically seat to it forming a sealed interface. A smooth contour to the perimeter of probe 40 would be advantageous. In one embodiment, the cross-sectional shape of the probe can be such that the seal bore can easily elastically seat to it to form a sealed interface. However, the applied force is not limited to being a solid object or a specific shape thereof, as the applied force could be created by a hollow object, such as a cannula, or the applied force could be a sufficient or predetermined pressure differential, for example, across seal 1 (i.e., the pressure difference between first and second spaces 21, 22). In the embodiment of a hollow object, fluid can pass through the object even while fluid is prevented from passing through an interface between an outer periphery of the object and seal 1.

Figure 5:
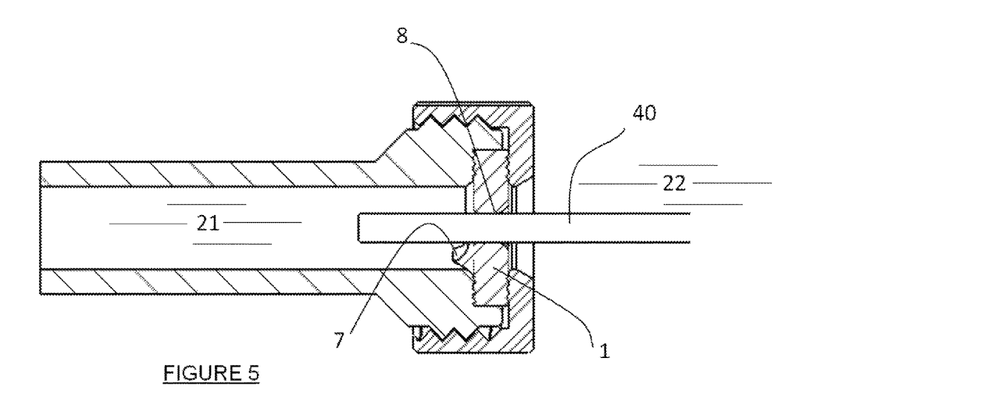
FIG. 5 is an axial half-section of the assembly of FIG. 1 wherein the interface is penetrated by an elongated object.
Figure 6:
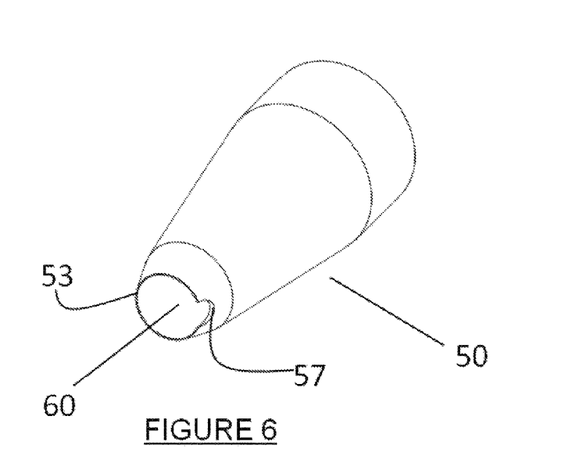
FIG. 6 is a perspective view of a perforating punch of one embodiment of the presently disclosed technology.
Figure 7:
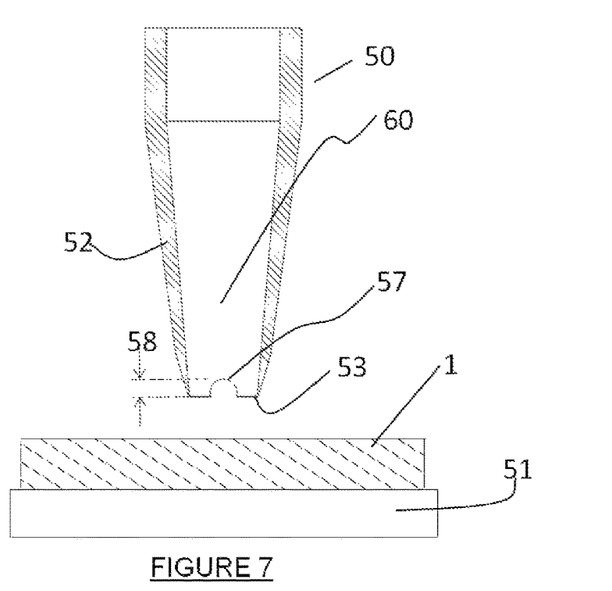
FIG. 7 is an axial half section view of the punch of FIG. 6 showing a base against which the punch can act.

FIG. 5 shows probe 40 having fully penetrated through bore 8. In one embodiment, when probe 40 is inserted into bore 8, tap 7 is elastically distorted rearwardly from its sealing position, protruding somewhat into first space 21, and bore 8 is stretched radially, constrictively sealing to probe 40. As probe 40 is withdrawn from bore 8, the structure of tap 7 causes it to follow the probe, thereby returning immediately to its sealing position within the bore, and simultaneously bore 8 elastically retracts to its unpenetrated diameter, thereby preventing the flow of fluid therethrough.

The force urging tap 7 to return fully into bore 8 as probe 40 is withdrawn can be provided by its inherent elasticity applied through connected portion 15 with seal 1. Unlike other elastomeric sealed barriers employing slitted seals, which rely on the elasticity of thin diaphragms to return to their sealed positions, the presently disclosed technology can have a much greater elastic force furnished by the substantial connection between tap 7 and the main body of seal 1.

Figure 9:
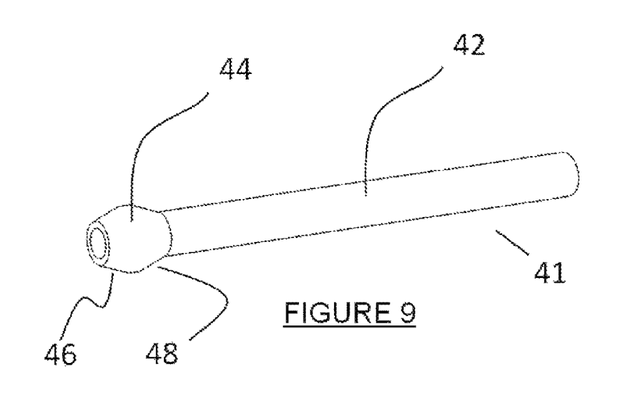
FIG. 9 is a perspective view of an alternate probe configuration having an enlarged tip portion.

Alternative probe configurations can be advantageous. An alternative probe 41 with shaft portion 42 and larger diameter tip 44 with tapered ends 46, 48, as shown in FIG. 9, can temporarily expand bore 8 to a diameter greater than the diameter of shaft portion 42 as the tip passes through it during both insertion and withdrawal. Upon withdrawal of alternate probe 41, the temporary expansion of bore 8 by tip 44 aids in sealably returning tap 7 with flared end segments 13, 14 into bore 8. Once fully penetrated, the diameter of bore 8 remains just that required to seal to shaft portion 42. Tip 44 also facilitates wiping bore 8 as alternate probe 41 is inserted and withdrawn.

In one embodiment, in order to be functional, the interface as shown in the unpenetrated condition of FIG. 4 must remain sealed even in the presence of a difference between the pressures in first and second spaces 21 and 22. In other words, to prevent leakage past the interface, tap 7 must remain in sealing position within bore 8 in the presence of a pressure differential across the interface. In this circumstance the presently disclosed invention functions much like a pressure relief valve, permitting flow only in response to an adequate or pre-defined pressure differential across it. The amount of pressure differential it must withstand before initiating flow depends on the application. The same comments apply when the interface is penetrated, as shown in FIG. 5, wherein the seal between the bore and the inserted probe must again be maintained in the presence of a pressure differential across the interface. Many medical uses for the presently disclosed technology require only very modest pressure differentials, often less than one atmosphere, for example, which are easily accommodated by the proposed structure in both the penetrated and unpenetrated conditions.

The pressure differential across the interface at which the presently disclosed technology will function properly can be determined by one or several controllable factors, such as seal outer diameter, seal thickness, bore diameter, tap shape, thickness of the connected portion, elastomer type and durometer, probe diameter, and the properties of the material to be transferred. Variations in these parameters allow the sealed penetrable interface to satisfy a wide range of common applications. The presently disclosed technology has been proven to maintain or preserve fluid separation between first and second spaces 21 and 22 even when the pressure differential between the two spaces has reached 35 pounds per square inch (PSI), for example.

Figure 8:
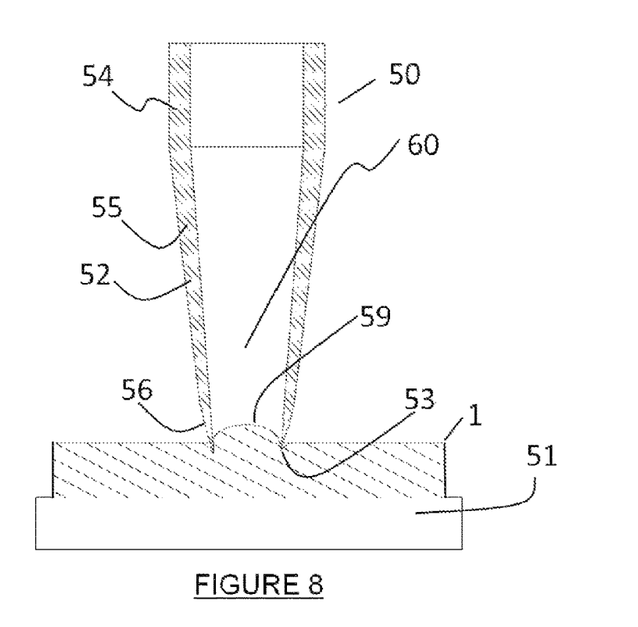
FIG. 8 is an axial half section view of the punch and base of FIG. 6, wherein the punch has partially penetrated a seal.

The method for cutting a perforation through an elastic barrier and resulting in a shaped, attached segment such as tap 7 is not easily discerned, but it is easily and quickly applied. In one embodiment, the method employs a hollow punch configured to produce the desired perforation. Referring to FIGS. 2 through 8, perforation 6 can be cut through seal 1 by forcing formed punch 50 (FIG. 6) through elastomeric seal 1 and against base 51, as illustrated in axial cutaway in FIG. 7. Punch 50 can include a partially or completely tapered, hollow body 52 terminating in sharpened end 53. As shown in FIG. 8, first portion 54 of body 52 can be cylindrical, second portion 55 of body 52 can be tapered at a first angle, and third portion 56 of body 52 can be tapered at a second angle greater than the first angle. Sharpened end 53 can include an unsharpened or smooth gap 57, which can be slightly cut away, raised or simply dulled depending on the desired configuration of uncut portion 15. Sharpened end 53 can extend around an entire periphery (e.g., circumference) of a free end of body 52, except for the portion where gap 57 is located. The gap is not limited to a particular size, shape or configuration, as the dimensioning of the gap can be modified to provide the desired functional properties.

In operation of one embodiment, as punch 50 penetrates the seal, sharpened end 53 eventually contacts base 51, cutting through seal 1 except for the portion of seal 1 engaged by gap 57. That portion is not completely cut through, leaving uncut seal portion 15. The radial extent of uncut portion 15 depends on the arc length of gap 57. The axial extent of uncut portion 15 depends on depth 58 (see FIG. 7) of gap 57. Depth 58 is measured along a longitudinal axis of punch 50 from a free end thereof. In the disclosed embodiment, gap 57 is deep enough to maintain uncut portion 15 completely through the thickness of seal 1. The diameter and shape of flared end 13 of tap 7 can depend on a number of factors, important among which is the sharpness of sharpened end 53.

FIG. 8 shows a cross-section of the punching process at the point where punch 50 is pressed into seal 1, but has not yet cut the seal. Portion 59 of seal 1 can protrude elastically into internal cavity or passageway 60 of punch 50. When punch 50 eventually cuts through seal 1, protruded portion 59 results in flared end 13 (FIG. 3) whose diameter is larger than that of central portion 12 of tap 7. A sharp end 53 results in relatively less protrusion than would occur if it were duller, and consequently creates a smaller diameter 13. Conversely, dulling cutting edge 53 creates a larger diameter flare. Flared end 14 of tap 7 is a result of the distortion of the elastomer as it is squeezed somewhat into cavity 60 of punch 50 just as punch 50 makes contact with base 51. The diameter of central portion 12 of tap 7 is determined in large measure by the diameter of sharpened end 53.

There are many factors in addition to those just mentioned which determine the exact shape of perforation 6, including but not limited to seal thickness and elasticity, sharpness of the cutting edge of the punch, and details of the unsharpened gap.

Many variations of the above method for making a shaped perforation are possible. For instance, the punch need not be of round cross-section, but instead could be oval or any other shape, such as those with smooth contours. Instead of the punch having an unsharpened gap, the base against which the punch acts could have an indentation, which would similarly leave an uncut portion similar to 15 in the example. To get a substantial flare on both ends of the tap, instead of having the punch act against a flat base as in the example, it could act against an opposing punch, wherein one or both of the punches could have an opposing gap in the sharpened end.

A prototype of the sealing structure as shown in FIG. 4 was created. Seal 1 was formed of pure gum rubber, 40 durometer Shore A. The seal outer diameter was 1.00 inches, and the seal had a thickness of 0.13 inches. The probe had a diameter of 0.17 inches. The bore and tap had cylindrical shapes with slightly flared ends. The bore and tap each had a diameter of 0.11 inches. On the high-pressure side, the flared-end diameter of the tap and the bore was 0.20 inches. Conversely, on the low pressure side, the flared-end diameter of the tap and bore was 0.17 inches. It is understood that the dimensions described above could be modified and still achieve the desired result of the presently disclosed technology. Tap water was contained in the first space 21, and air was contained in the second space 22. The pressure within the first spaced exceeded the pressure within the second space 22 by 1 atmosphere. The probe was lightly lubricated with silicone oil prior to the first insertion.

During a series of ten insertions and withdrawals of the probe, the prototype experienced no leakage before insertion, no leakage during insertion, and no leakage after withdrawal. The above test series was repeated three times with the same results.

The above disclosed method and description of generic embodiments of the presently disclosed technology are provided to enable any person skilled in the art to make or use the presently disclosed technology. Various modifications to the embodiments will be readily apparent to those skilled in the art, and the generic principles described herein can be applied to other embodiments without departing from the spirit or scope of the presently disclosed technology. Thus, it is to be understood that the description and drawings presented herein represent a functional generic embodiment of the presently disclosed technology and are therefore representative of the subject matter which is broadly contemplated by the presently disclosed technology. It is further understood that the scope of the presently disclosed technology fully encompasses other embodiments that may become obvious to those skilled in the art and that the scope of the presently disclosed technology is accordingly limited by nothing other than the appended claims.

What is claimed is:

1. A penetrable interface configured to separate two or more spaces, the interface comprising:
    an elastomeric seal having a bore and a tap, at least a portion of the tap having a cylindrical shape, the tap having a central portion attached to an uncut portion of the elastomeric seal, the central portion of the tap being integrally formed with the uncut portion, the tap including a first flared portion, the bore and the tap creating a sealing engagement therebetween in the absence of an applied force on the tap, the uncut portion providing an elastic force to return the tap to an at-rest or initial position within the bore in the absence of an applied force on the tap, and the bore and the tap being distorted out of sealing engagement when subjected to an applied force on the tap.

2. The penetrable interface of claim 1, wherein the applied force is a pressure differential across the interface.

3. The penetrable interface of claim 1, wherein the applied force is created by a rigid object.

4. The penetrable interface of claim 1, wherein the tap returns to a sealing position within the bore when the applied force is removed.

5. The penetrable interface of claim 1, wherein a crescent-shaped perforation defines the interface between the bore and the tap.

6. The penetrable interface of claim 1, wherein the first flared portion is spaced-apart from a second flared portion.

7. The penetrable interface of claim 1, wherein the tap is defined by a perforation between the bore and the tap.

8. The penetrable interface of claim 1, wherein the tap is configured to move with respect to the bore.

9. The penetrable interface of claim 1, wherein the bore and the tap are two distinct segments of the elastomeric seal.

10. A penetrable interface configured to separate two or more spaces, the interface comprising:
    an elastomeric seal having a first segment and a second segment, a portion of the second segment being integrally formed with a portion of the first segment, the first and second segments creating a sealing engagement therebetween in the absence of an applied force on the second segment, and the first and second segments being distorted out of sealing engagement when subjected to an applied force on the second segment, wherein the second segment includes a first flared end portion spaced-apart from a second flared end portion, each flared end portion being configured to aid in centering the second segment within the first segment.

* * * * *